US00PP13796P39

(12) United States Plant Patent
Pieters

(10) Patent No.: US PP13,796 P3
(45) Date of Patent: May 13, 2003

(54) CHRYSANTHEMUM PLANT NAMED 'GEDI ONE NOV'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,960

(22) Filed: Jun. 4, 2001

(65) Prior Publication Data

US 2002/0184684 P1 Dec. 5, 2002

(51) Int. Cl.[7] ..... A01H 5/00
(52) U.S. Cl. ..... Plt./290
(58) Field of Search ..... Plt./290, 287

(56) References Cited

U.S. PATENT DOCUMENTS

PP10,216 P 1/1998 Pieters ..... Plt./290
PP11,569 P 10/2000 Pieters ..... Plt./290

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large decorative type inflorescence, consistent flowering response to short days, blooming consistently after 49 days of short day length, free branching habit, bicolor blooms, very uniform round growth habit, and a large quantity of blooms per flowering branch.

1 Drawing Sheet

LATIN NAME

*Dendranthema morifolium.*

VARIETY

Figure 1:
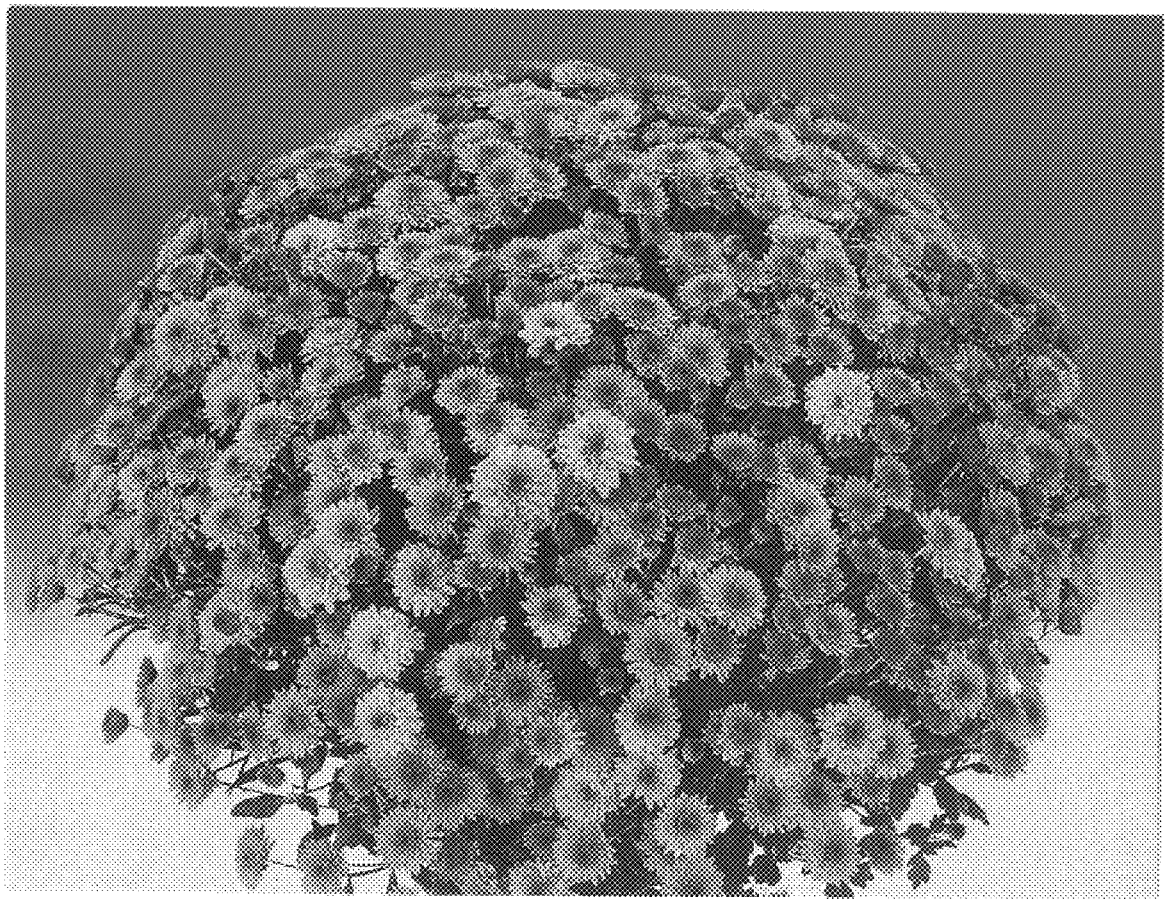

'GEDI ONE NOV'.

BACKGROUND OF THE INVENTION

The present invention relates to a new and distinct cultivar of Chrysanthemum plant, botanically known as *Dendranthema morifolium* and herein after referred to by the cultivar name 'GEDI ONE NOV.'

This new cultivar was the result of hybridization of a female parent, 'Bronia' (unpatented in the United States) with a male parent, 'Gedi ORO8' (U.S. Plant Pat. No. 11,569). The new cultivar was selected in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE NOV' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE NOV.' These observations were made on plants approximately 120 days old from rooted cuttings. These characteristics in combination distinguish 'GEDI ONE NOV' as a new and distinct Chrysanthemum:

1. Large decorative type inflorescence;
2. Consistent flowering response to short days, blooming consistently after 49 days of short day length;
3. Free branching habit;
4. Bicolor blooms;
5. Very uniform round growth habit; and
6. Large quantity of blooms per flowering branch.

Plants of the new Chrysanthemum are similar to plants of the parent cultivars in most horticultural characteristics. However, the comparison variety 'Gedi ORO8', U.S. Plant Pat. No. 11,569, is decorative with an open center, frequently showing disc florets. The new variety is completely decorative, not opening to show any center or disc florets.plants of the new cultivar differ from plants of the female parent cultivar 'Bronia' in the following characteristics:

1. The new cultivar naturally blooms 2 weeks earlier;
2. The new cultivar has different color ray florets; and
3. The new cultivar has larger diameter flowers.

The new cultivar also differed from the male parent 'Gedi ORO8' in the following characteristics:

1. The new cultivar has an different ray floret color;
2. The new cultivar has a different flower type;
3. The new cultivar naturally blooms 2 weeks earlier;
4. The new cultivar has larger diameter blooms.

The new cultivar can be compared to the Chrysanthemum cultivar 'Aldo' (disclosed in U.S. Plant Pat. No. 10,216). Different growing conditions sometimes produce different results. In the growing trial from which the new variety was compared to 'Aldo', U.S. Plant Pat. No. 10,216, the new variety produced an average of 14 blooms per flowering branch while 'Aldo' on average produced 10. However plants of the new Chrysanthemum differed from the plants of the cultivar 'Aldo' in the following characteristics:

1. New cultivar has larger diameter blooms;
2. New cultivar has more ray florets;

3. New cultivar has a more round plant shape and greater branching; and
4. New cultivar has more blooms per flowering branch.

BRIEF DESCRIPTION OF THE PHOTOGRAPHS

The photograph shows a plant of 'GEDI ONE NOV' grown in a 2 gallon container. One cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'GEDI ONE NOV'
Commercial classification: Garden-type Chrysanthemum
Parentage: Hybridization of female parent 'Bronia' and male parent 'Gedi ORO8'

PROPAGATION

Time to rooting: 7 to 14 days at approximately 21° C.
Root description: Fine, fibrous

PLANT

Growth habit: Mounding herbaceous perennial
Height: Approximately 28 cm
Plant spread: Approximately 34 cm.
Growth rate: Moderate
Branching characteristics: Free Branching
Internode length: Approximately 2.2 cm.
Length of lateral branches: Approximately 23 cm
Number of leaves per lateral branch: Approximately 24
Stem color: Near 137A

FOLIAGE

Leaf:
*Arrangement.*—Alternate, single.
*Average length.*—Approximately 7.6 cm.
*Average width.*—Approximately 4.5 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.

Color:
*young foliage upper side.*—Near 137A.
*young foliage under side.*—Near 137B.
*mature foliage upper side.*—Near 137A.
*mature foliage under side.*—Near 137B.
*venation upper side.*—Near 138C.
*venation under side.*—Near 137C.

Petiole:
*Average length.*—Approximately 2.9 cm.
*Color.*—Near 137A.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the first two weeks of September.
*Number of inflorescences per stem.*—Approximately 14.
*Inflorescence diameter.*—Approximately 6.5 cm.
*Inflorescence depth.*—2.1 cm.
*Inflorescence longevity on plant.*—Approximately 24–28 days.
*Persistence.*—Persistent.

Ray florets:
*Appearance.*—Matte.
*Texture.*—Smooth.
*Average number per flower.*—280.
*Shape.*—Oblanceolate.
*Margin.*—Entire.
*Apex.*—Obtuse.
*Length.*—Approximately 3.8 cm.
*Width.*—Approximately 1.1 cm.
*Color.*—upper surface at first opening: Near 178A upper surface at maturity: Near 24B upper surface at fading: Near 21C under surface at first opening: Near 178A under surface at maturity: Near 23B under surface at fading: Near 21C.
*Center ray florets color.*—Near 178A throughout maturity and fading.

Disc florets:
*Appearance.*—Shiny.
*Texture.*—Smooth.
*Average number per flower.*—Approximately 30.
*Shape.*—Cylindric.
*Apex.*—Obtuse.
*Average length.*—Approximately 1 cm.
*Average width.*—Approximately 0.1 cm.
*Color.*—at first opening: Near 2A at maturity: Near 21A at fading: Near 17D.

Peduncle:
*Length.*—at terminal end (shortest): Approximately 7 cm at lateral end (longest): Approximately 12 cm.
*Diameter.*—Approximately 0.3 cm.
*Strength.*—Moderate.
*Color.*—Near 137C.
*Habit.*—Erect.
*Surface texture.*—Lightly pubescent.

Inflorescence bud:
*Length.*—Approximately 1 cm.
*Diameter.*—Approximately 1 cm.
*Form.*—Globular.
*Color.*—Near 178A.

Phyllaries:
*Appearance.*—Matte.
*Texture.*—Lightly pubescent.
*Number.*—Approximately 30 to 40.
*Shape.*—Ovate.
*Margin.*—Entire.

*Apex.*—Acute.
*Diameter.*—Approximately 0.4 cm.
*Length.*—Approximately 0.6 cm.
*Color.*—upper side: Near 137A under side: Near 137A.

REPRODUCTIVE ORGANS

Ray florets:
*Number of pistils per flower.*—1.
*Stigma shape.*—2 branched.
*Stigma color.*—Near 16D.
*Style color.*—Near 16D.
*Style length.*—Approximately 0.6 cm.

Disc florets:
*Number of pistils per flower.*—1.
*Stigma shape.*—Cylindric.
*Style length.*—0.5 cm.
*Number of stamens per flower.*—Approximately 5.
*Anther shape.*—Tubular.
*Anther color.*—Near 16A.
*Pollen color.*—Near 17B.

OTHER CHARACTERISTICS

Seed production: Commercially, this plant is not used or observed in a stage wherein seeds would be produced. Therefore, seed production has not been observed.

Flower fragrance: Absent

Disease resistance: Neither resistance nor susceptibility to diseases and pests have been observed in this cultivar.

What is claimed is:

1. A new and distinct variety of Chrysanthemum plant named 'GEDI ONE NOV' as herein illustrated and described.

* * * * *